United States Patent [19]

Ferraris et al.

[11] Patent Number: 5,110,798
[45] Date of Patent: May 5, 1992

[54] PURINE DERIVATIVES HAVING PHARMACOLOGICAL ACTION

[75] Inventors: Paolo C. Ferraris, Genoa; Riccardo Stradi, Milan, both of Italy

[73] Assignee: Co Pharma Corporation S.r.l., Genoa, Italy

[21] Appl. No.: 397,457

[22] PCT Filed: Dec. 22, 1988

[86] PCT No.: PCT/EP88/01194

§ 371 Date: Aug. 10, 1989

§ 102(e) Date: Aug. 10, 1989

[87] PCT Pub. No.: WO89/05818

PCT Pub. Date: Jun. 29, 1989

[30] Foreign Application Priority Data

Dec. 24, 1987 [IT] Italy ................. 23218 A/87

[51] Int. Cl.$^5$ ................. A61K 37/02; A61K 31/62; C07K 5/06
[52] U.S. Cl. ................. 514/19; 514/18; 514/261; 530/331
[58] Field of Search ............... 514/18, 19, 261; 530/331; 562/559, 575

[56] References Cited

U.S. PATENT DOCUMENTS 4,548,819  10/1985  De Clercq et al. ............. 514/261

FOREIGN PATENT DOCUMENTS 0077460  4/1983  European Pat. Off. .

OTHER PUBLICATIONS

G. Migliorati et al., *Cancer Detection and Prevention 16:* 1-3, 16 Apr. 1991.

*Primary Examiner*—Robert A. Wax
*Assistant Examiner*—Stephen Walsh
*Attorney, Agent, or Firm*—Bucknam and Archer

[57] ABSTRACT

Compounds of formula I

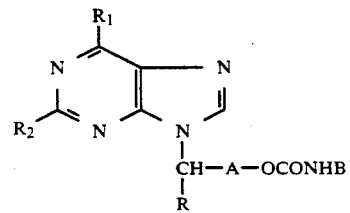

wherein $R_1$ is OH or $NH_2$ and $R_2$ is H or $NH_2$, R is H or lower alkyl, A is an alkyl chain optionally interrupted by heteroatoms and B is an amino acid, a di- or tri-peptide, are useful in human therapy.

2 Claims, No Drawings

PURINE DERIVATIVES HAVING PHARMACOLOGICAL ACTION

The present invention relates to purine derivatives having an immunomodulating, antiviral activity and on Central Nervous System, to a process for the preparation thereof and to pharmaceutical compositions containing them.

The derivatives according to the invention can be presented by the following tautomeric general formula I

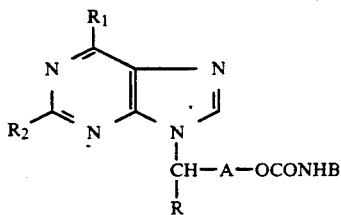

wherein $R_1$ is OH or $NH_2$ and $R_2$ is hydrogen or $NH_2$, with the proviso that $R_1$ and $R_2$ cannot be both $NH_2$ groups, R is hydrogen or $C_1$-$C_6$ alkyl, A is a group of formula II $$-(CH_2)_m-X-(CH_2)_n- \qquad (II)$$

or a group of formula

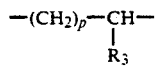   (III)

wherein X is oxygen, sulphur or selenium
m is an integer from 0 to 4;
n is an integer from 2 to 4;
p is an integer from 0 to 8;
$R_3$ is hydrogen or $C_1$-$C_6$ alkyl;
B is a residue of a natural amino acid of the l, d or dl series or a di- or tri-peptide residue in which the amino acids which compose it are selected from the group consisting of alanine, arginine, glycine, isoglutamine, leucine, lysine, methionine, ornithine, proline and serine, with the proviso that, when A is a residue of formula III, B is always a di- or tri-peptide residue as above defined.

In case amino acid B or N-terminal amino acid of the di- or tri-peptide is a basic amino acid (arginine, ornithine, lysine), the carbamate bond can involve either the amino group which is at the l-position to the carboxy group or the amino group at the w-position to the carboxy group.

The present invention also relates to non toxic salts of compounds of formula I.

European patent N. 0 077 660 discloses purine derivatives in which an amino acid is linked to the purine ring at the 9-position by means of carbonyloxyalkyl or carbonylethylcarbonyloxyalkyl bridges.

The derivatives according to the present invention show, in comparison to the known compounds, a different and surprising pharmacological activity range, particularly immunostimulating activity, antiviral activity and activity on Central Nervous System, so that they are valuable for use in human therapy.

Preferred compounds according to the invention are:
(a) compounds in which R is hydrogen, A is a group of formula II wherein m is 0 or 1, X is oxygen, n is 2 and B is an amino acid residue selected from the group consisting of arginine, methionine, leucine or the residue of a di- or tri-peptide selected from the group consisting of leucyl-methionine, ornithyl-ornithine, glycyl-leucyl-methionine, leucyl-seryl-arginine, lysyl-arginine, alanyl-isoglutamine, lysyl-lysine, histidyl-leucyl-methionine, propyl-arginine;
(b) compounds in which R is hydrogen, A is a residue of formula III in which p is 2 or 3, $R_3$ is hydrogen and B is a di- or tri-peptide selected from the above defined group.

Compounds I are prepared by reaction of a compound of formula IV:

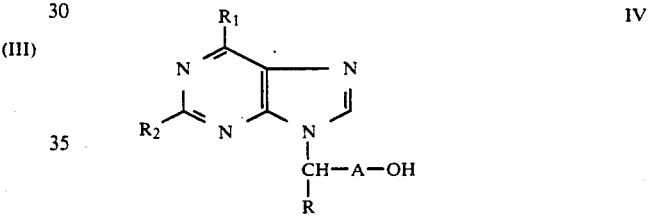

wherein $R_1$, $R_2$, R and A are as above defined, with phosgene and subsequent condensation with an amino acid or di or tri-peptides of formula $H_2NB$ according to per se known procedures.

Compounds of formula IV in which $R_1$ is OH, $R_2$ is hydrogen or $NH_2$ and A is a residue of formula III wherein R and $R_3$ are hydrogen, are prepared according to the procedures described in EP-B-77460. Compounds IV wherein $R_1$ is OH, $R_2$ is hydrogen and A is a residue of formula III can be prepared according to the process described in Italian Pat. Application N. 19083 A/87.

Compounds IV in which $R_1$ is OH and $R_2$ is $NH_2$ can be obtained according to the following reaction scheme:

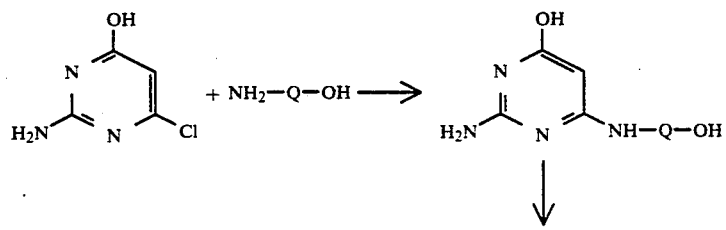

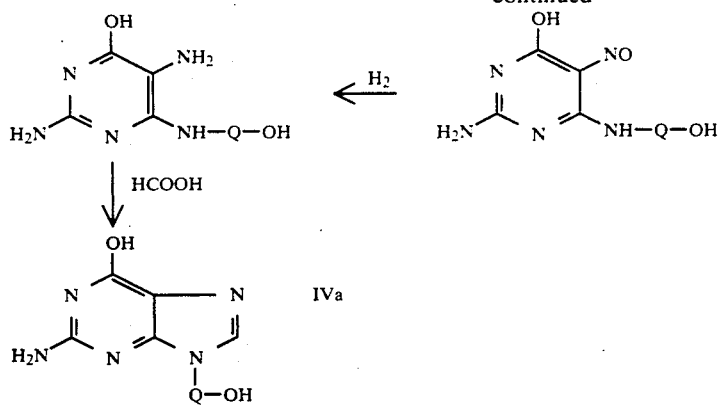

wherein Q is a residue of formula

in which R and A are as above defined.

Compounds IV in which $R_2$ is hydrogen and $R_1$ is $NH_2$, on the contrary, are obtained from compounds of formula V

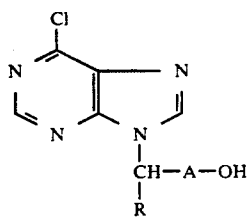

wherein R and A are as above defined, by reaction with liquid $NH_3$ at high temperature.

For the preparation of compounds IV in which A is a residue of formula II, reaction schemes analogous to the ones reported above and the ones known for the preparation of purine systems can be conveniently used. Thus, for example, 4,6-dichloro-5-amino-pyrimidine can be reacted with a compound for formula $H_2N(CH_2)_m$—X—$(CH_2)_nOH$ wherein X, m and n are as above defined, to obtain the intermediates of formula VI:

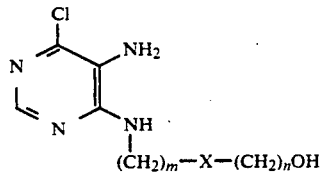

which can then be transformed into corresponding compounds I by means of an appropriate combination of known reactions, analogous to the above reported ones and anyhow known to those skilled in the art.

The following examples further illustrate the invention without limiting its spirit and scope.

EXAMPLE 1

N-[N-[5-(hypoxanthin-9-yl)pentyloxycarbonyl]-L-leucyl]-L-methionine

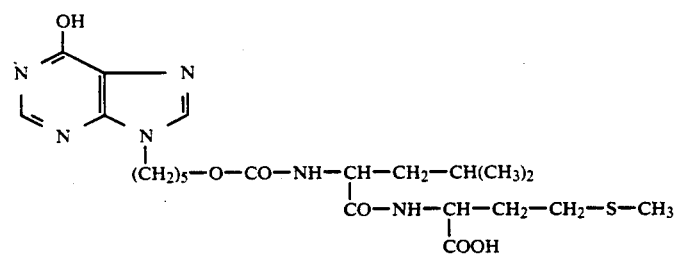

0.850 g (0.0032 mole) of leucyl-methionine and 0.824 g (0.0096 mole) of sodium bicarbonate were dissolved in 40 ml of bidistilled water, in a 150 ml flask. To the resulting aqueous solution, having pH=8, a suspension of 1.05 g (0.0032 mole) of 9-[5-chlorocarbonyloxy)pentyl]hypoxanthine hydrochloride in 40 ml of toluene was added in ice bath.

The reaction mixture was left to react at room temperature under magnetic stirring for 5 hours. After that the two phases were separated; the solvent was evaporated from the aqueous phase to obtain 1.8 g of crude compound which was chromatographed on a silica gel column using as the eluent first a 1:1 ethyl acetate/ethanol mixture, then methanol. 1.450 g of compound were thus obtained.

|   | theorical | found |
|---|-----------|-------|
| C | 51.75 | 51.82 |
| H | 6.71 | 6.70 |

-continued

| | theorical | found |
|---|---|---|
| N | 16.45 | 16.38 |

EXAMPLE 2

N²-[N⁵-[5-(hypoxanthin-9-yl)pentyloxycarbonyl]-L-ornithil]-L-ornithine and

N⁵-[5-(hypoxanthin-9-yl)pentyloxycarbonyl]-N²-L-ornithil-L-ornithine

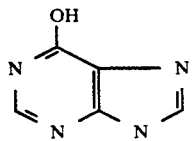

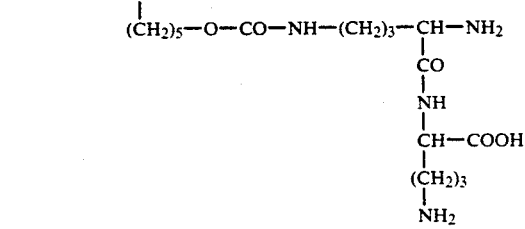

A

+

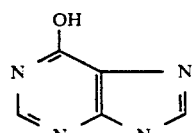

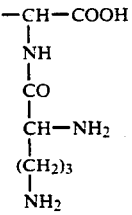

B

To a suspension of 1,05 g (0.0032 mole) of 9-(5-chlorocarbonyl-oxy-pentyl)-hypoxanthine hydrochloride in 40 ml of toluene, a solution of 1.68 g (0,0032 mole) di ornithyl-ornithine monohydrochloride-trihydrobromide and 1,9 g (0,0224 mole) of sodium bicarbonate in bidistilled water at pH=8 was added, under magnetic stirring in ice bath. When the addition was over the reaction mixture was left to stand for 20 hours at room temperature. Controls were carried out by TLC (Thin Layer Chromathography), using methanol as the eluent. At the end of the reaction the two phases were separated, the aqueous phase was evaporated under vacuum and the resulting crude compound was chromatographed on silica gel, using methanol as the eluent. The mixture of the two products was thereby obtained, which products were separated by means of preparative HPLC.

| | theorical | found | found |
|---|---|---|---|
| C | 51,03 | 51,06 | 50,98 |
| H | 6,87 | 6,89 | 6,81 |
| N | 22,66 | 22,65 | 22,63 |

EXAMPLES 3-9

The compounds hereinbelow reported were obtained by means of an analogous process, using corresponding amounts of the appropriate peptide.

EXAMPLE 3

N-[N-[N-[5-(hypoxanthin-9-yl)pentyloxycarbonyl]-glycyl]-L-leucyl-methionine

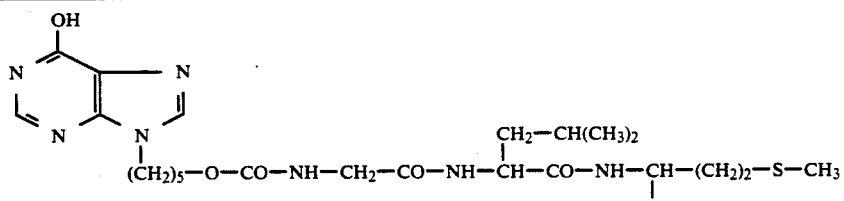

E.A. for C₂₄H₃₇N₇O₇S        MW = 567,24

| | theorical | found |
|---|---|---|
| C | 50,81 | 50,77 |
| H | 6,52 | 6,59 |
| N | 17,27 | 17,22 |

EXAMPLE 4

N²-[N[N-[5-(hypoxanthin-9-yl)penthyloxycarbonyl]-L-leucyl]-L-seryl-arginine

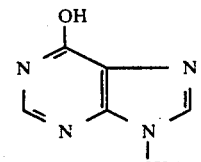

(CH₂)₅—O—CO—NH—CH—CO—NH—CH—CO—NH—CH—(CH₂)₃—NH—C(=NH)—NH₂ with side chains: CH₂—CH—(CH₃)₂ ; CH₂OH ; COOH

E.A. for C₂₆H₄₂N₁₀O₈    MW = 622.596

|   | theorical | found |
|---|---|---|
| C | 50,15 | 50,12 |
| H | 6,79 | 6,73 |
| N | 22,48 | 22,44 |

EXAMPLE 5

N²-[N⁶-[5-(hypoxanthin-9-yl)pentyloxycarbonyl]-L-lysyl]-L-arginine and

N²-[N²-[5-hypoxanthin-9-yl)pentyloxycarbonyl]-L-lysyl]-L-arginine

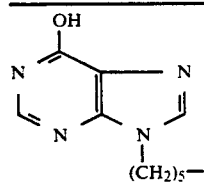

(CH₂)₅—O—CO—NH—(CH₂)₄—CH(NH₂)—CO—NH—CH(COOH)—(CH₂)₃—NH—C(=NH)—NH₂

+

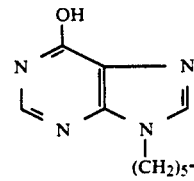

(CH₂)₅—O—CO—NH—CH—(CH₂)₄—NH₂
                |
                CO
                |
                NH
                |
                CH—COOH
                |
                (CH₂)₃
                |
                NH
                |
                C(=NH)—NH₂

E.A. for C₂₃H₃₈N₁₀O₆    MW = 550,544

|   | theorical | found | found |
|---|---|---|---|
| C | 50,17 | 50,19 | 50,16 |
| H | 6,95 | 6,89 | 6,93 |
| N | 25,42 | 25,39 | 25,44 |

EXAMPLE 6

N²-[N-[5-(hypoxanthin-9-yl)pentyloxycarbonyl]-L-alanyl]-L-isoglutamine

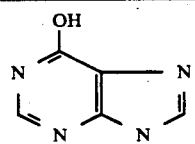

(CH₂)₅—O—CO—NH—CH(CH₃)—CO—NH—CH(CONH₂)—CH₂—CH₂—COOH

E.A. for C₁₉H₂₇N₇O₇    MW = 465,406

|   | theorical | found |
|---|---|---|
| C | 49,03 | 49,00 |
| H | 5,84 | 5,87 |
| N | 21,05 | 21,06 |

EXAMPLE 7

$N^2$-[$N^6$-[5-(hypoxanthin-9-yl)pentyloxycarbonyl]-L-lysyl]-L-lysine and $N^6$-[5-(hypoxanthin-9-yl)pentyloxycarbonyl]-$N^2$-L-lysyl-L-lysine E.A. for $C_{23}H_{38}N_8O_6$    MW = 522,534

|   | theorical | found | found |
|---|-----------|-------|-------|
| C | 52,86     | 52,89 | 52,84 |
| H | 7,33      | 7,31  | 7,29  |
| N | 21,43     | 21,40 | 21,45 |

EXAMPLE 8

N-[N-[$N^2$-5-(hypoxanthin-9-yl)pentyloxycarbonyl]-L-histidyl]-L-leucyl-L-methionine E.A. for $C_{28}H_{41}N_9O_7S$    MW = 647,608

|   | theorical | found |
|---|-----------|-------|
| C | 51,92     | 51,88 |
| H | 6,38      | 6,35  |
| N | 19,45     | 19,47 |

EXAMPLE 9

[N-[(hypoxanthin-9-yl)pentyloxycarbonyl]prolyl]-arginine

E.A. for $C_{22}H_{33}N_9O_6$    MW = 519,484

|   | theorical | found |
|---|-----------|-------|
| C | 50,86     | 50,83 |

| H | 6.40 | 6.41 |
| N | 24.25 | 24.29 |

EXAMPLE 10

Preparation of $N^2$-[2-[2-(hypoxanthin-9yl)ethoxy]-ethoxy-carbonyl]arginine a) Preparation of 4-chloro-5-amino-6-[(2-(2-hydroxyethoxy)-ethyl]amino-pyrimidine.

508 ml di n-pentanol, 25 g (0,152 mole) of 4,6-dichloro-5-aminopyrimidine, 36,25 ml (0.152 mole) of tributylamine, 11 ml (0,152 mole) of 2-(2-aminoethyoxy)ethanol and KI in catalytic amounts were placed into a three neck flask provided with reflux condenser and mechanical stirrer, for 24 hours. The progress of the reaction was checked by TCL, using ethyl acetate as the eluent. At the end of the reaction pentanol was evaporated under reduced pressure and the resulting crude reside was chromatographed on silica gel using 9:1 chloromethane/ethanol as the eluent.

The compound was crystallized from ethyl acetate. M.P.=121° C.

b) Preparation of 9-[2-(2-hydroxyethoxy)ethyl]-hypopxanthine.

10 g (0,043 mole) of compound a) in 150 ml of formic acid were placed into a 250 ml flask. The reaction was refluxed for 24 hours. The progress of the reaction was controlled by TLC using 8:2 ethanol/triethylamine as the eluent.

AT the end of the reaction, formic acid was evaporated under reduced pressure and the residue was crystallized from ethanol.

Reaction yield: 55%.
M.P.>200° C.

c) Preparation of 9-[2-[2-chlorocarbonyloxy)ethoxy]ethyl]-hypoxanthine hydrochloride.

3 g (0,0133 mole) of compound b) were reacted with 30 ml of 20% phosgene in toluene in 80 ml of anhydrous toluene, under magnetic stirring. It is advisable to drop the phosgene solution. The reaction was controlled by TLC using ethyl acetate/ethanol in 1:1 ratio as the eluent. In order to visualize the product in the plate, a reaction sample was treated with a tert-butylamine excess to obtain corresponding urethane. At the end of the reaction solvent was evaporated off under reduced pressure to obtain the crude product which was directly reacted for:

d) preparation of $N^2$-[2-[2-(hypoxanthin-9-yl)-ethoxyethoxy-carbonyl]arginine.

0,927 g (0,0053 mole) of L-arginine was dissolved in 10 ml of water, under magnetic stirring. 0,86 g (0,002 mole) of compound C, suspended in 10 ml of toluene, was added to the above solution. The reaction mixture was left under magnetic stirring for 5 hours.

At the end of the reaction the two phases were separated and the aqueous phase was evaporated under reduced pressure. The resulting crude residue was purified on a silica gel column, using methanol as the eluent. 0,5 g of compound was obtained.

EXAMPLE 11

Using 2-(2-aminoethyl)thio)ethanol, by means of a process analogous to the above one, the following compound was prepared:

$N^2$-[2-[2-(hypoxanthin-9-yl)-ethylthio]ethoxycarbonyl]-L-arginine, according to the following reaction scheme:

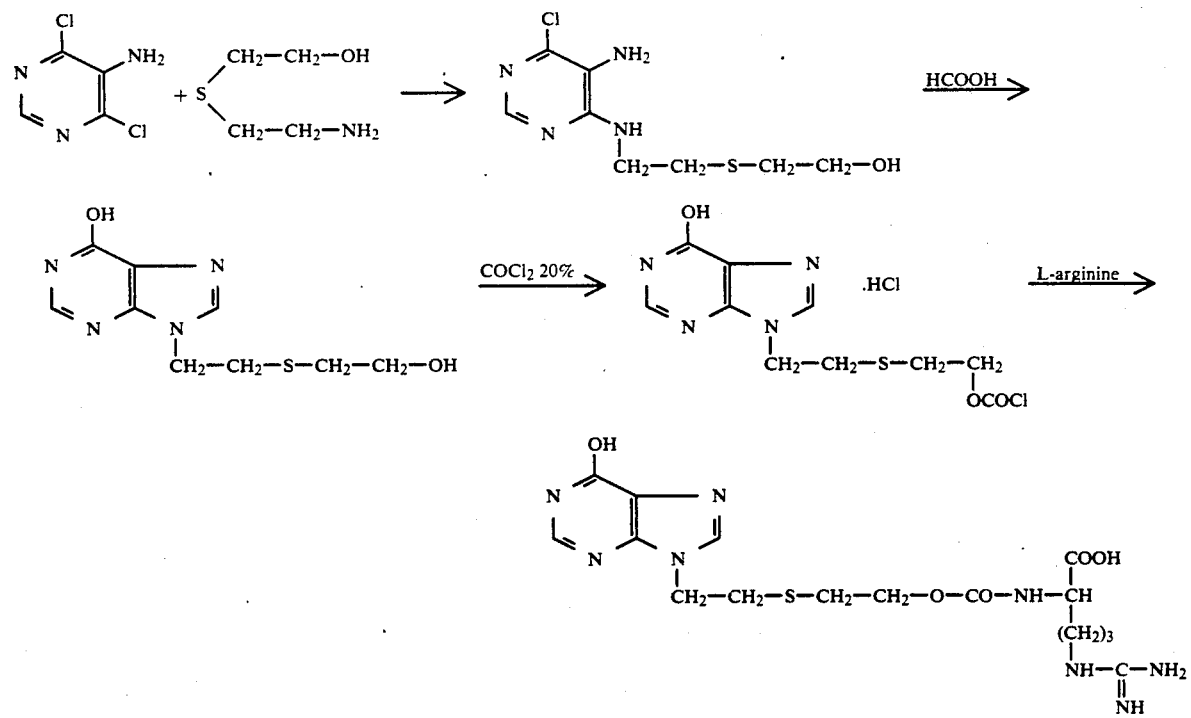

Biological activity of the above exemplified compounds was studied, and the compounds according to the invention proved to be active as immunomodulators, neurotransmitters and antiviral agents. Particularly, the compounds of the invention turned out to be active in the following tests, showing an interaction on the immunosystem:

a) in vitro generation of Natural Killer cells from bone marrow precursors;
b) in vivo boosting of Natural Killer cells activity;
c) in vitro cytotoxicity against YAC-1 target cells:
d) transplant of bone marrow in mice;
e) macrophages activation.

Some of the compounds of the invention (example 3 and analogous), showed neurokinin-like activity in several in vitro models. They possibly act on neurokinin receptors such as NK-P, NK-A and NK-B.

Moreover, the compounds of the invention proved to be active in in vitro antiviral activity tests on Vescicula Stomatitis Virus (VSV) and on encephalomyocarditis in L929 cells.

From what has been above reported, it is evident that the compounds of the invention can be advantageously used in human therapy of diseases having viral, tumor and bacterial origin, of neurologic syndromes or different pathologies in which immunosystem is recognizedly involved.

The present invention also relates to all the industrially applicable aspects related to the use of compounds I as therapeutical gent. Thus, an essential object of the invention is provided by pharmaceutical compositions containing as the active ingredient compounds I alone or in admixture with a pharamaceutical carrier, in form of tablets, sugar-coated pills, capsules, powders, granules for reconsititution in oral solutions or suspensions, syrups, injection vials, etc.

The active ingredients can be alone in capsules. Otherwise, they can be formulated using traditional pharmaceutical carriers, for example excipients such as lactose or talcum, granulation agents such as methylcellulose and/or surface active agents such as polyoxyethylene stearate; preservatives such as ethyl p-hydroxybenzoate and possibley flavoring agents.

The pharmaceutical compositions of the present invention can preferably be formulated in form of unitary dosage containing 1 to 1000 mg of a compound of formula I in admixture with a pharmaceutical carrier. Said unitary doses can be administered one to more times a day, depending on the pathology and the conditions of the patient.

We claim:

1. A compound selected from the group consisting of:
   N-[N-5-(hypoxanthin-9-yl)pentyloxycarbonyl]-L-leucyl]-L-methionine;
   $N^2$-[$N^5$-[5-(hypoxanthin-9-yl)pentyloxycarbonyl]-L-ornithyl]-L-ornithine;
   $N^5$-[5-hypoxanthin-9-yl)pentyloxycarbonyl]-$N^2$-L-ornithyl-L-ornithine;
   N-[N-[N-[5-(hypoxanthin-9-yl)pentyloxycarbonyl]-glycyl]-L-leucyl-methionine;
   $N^2$-[N-[N-[5-(hypoxanthin-9-yl)penthyloxycarbonyl]-L-leucyl]-L-seryl-arginine;
   $N^2$-[$N^6$-[5-(hypoxanthin-9-yl)pentyloxycarbonyl]-L-lysyl]-L-arginine;
   $N^2$-[$N^2$-[5-(hypoxanthin-9-yl)penthyloxycarbonyl]-L-lysyl]-L-arginine;
   $N^2$-[N-[5-(hypoxanthin-9-yl)pentyloxycarbonyl]-L-alanyl]-L-isoglutamine;
   $N^2$-[$N^6$-[5-(hypoxanthin-9-yl)pentyloxycarbonyl]-L-lysyl]-L-lysine;
   $N^6$-[5-(hypoxanthin-9-yl)penthloxycarbonyl]-$N^2$-L-lysyl-L-lysine;
   N-[N-[$N^2$-[5-(hypoxyanthin-9-yl)penthyloxycarbonyl]-L-histidyl]-L-leucyl-L-methionine;
   $N^2$-[N-[5-(hypoxanthin-9-yl)pentyloxycarbonyl]-L-proly]-L-arginine;

2. The method of treating a subject affected by leukemia or a solid tumor or a subject in need of bone marrow transplant which consists of administering to said subject the compound N-/N-[5-(hypoxanthin-9-yl)pentyloxycarbonyl]-L-leucyl]-L-5 methionine.

* * * * *